United States Patent
Einarsson

(10) Patent No.: US 7,094,058 B2
(45) Date of Patent: Aug. 22, 2006

(54) EDUCATIONAL PROSTHESIS DEVICE AND METHOD FOR USING THE SAME

(75) Inventor: Pálmi Einarsson, Kópavogur (IS)

(73) Assignee: Ossur hf, Reykjavik (IS)

( * ) Notice: Subject to any disclaimer, the term of this patent is extended or adjusted under 35 U.S.C. 154(b) by 368 days.

(21) Appl. No.: 10/219,286

(22) Filed: Aug. 16, 2002

(65) Prior Publication Data
US 2004/0034436 A1  Feb. 19, 2004

(51) Int. Cl.
*A63B 69/00* (2006.01)
(52) U.S. Cl. ...................................... 434/257
(58) Field of Classification Search ............ 434/247, 434/262, 365, 267, 118, 257
See application file for complete search history.

(56) References Cited

U.S. PATENT DOCUMENTS

| | | | | |
|---|---|---|---|---|
| 4,685,925 A | * | 8/1987 | Childress et al. | 623/25 |
| 5,413,611 A | | 5/1995 | Haslam, II et al. | |
| 5,443,525 A | | 8/1995 | Laghi | |
| 5,571,205 A | * | 11/1996 | James | 623/24 |
| 5,573,501 A | | 11/1996 | Ruscito et al. | |
| 5,679,004 A | * | 10/1997 | McGowan et al. | 434/247 |
| 5,899,855 A | * | 5/1999 | Brown | 600/301 |
| 6,535,793 B1 | * | 3/2003 | Allard | 700/259 |
| 2003/0222109 A1 | * | 12/2003 | Weiss | 224/222 |

OTHER PUBLICATIONS

Aitken, George T., M.D., "The Child Amputee An Overview", Journal of the Association of Children's Prosthetic-Orthotic Clinics, JACPOC Library, 1984, vol. 19, No. 2, pp. 23, http://jacpoc/oandp.com/library/1984_02_023.asp.
Rubenfeld, Lori Ann, et al., "Variables Influencing Self-Esteem in Children with Congenital or Acquired Limb Deficiencies", Journal of the Association of Children's Prosthetic-Orthotic Clinics, JACPOC Library, 1988, vol. 23, No. 4, pp. 85; http://jacpoc.oandp.com/library/1988_04_085.asp.
Design Academy EINDHOVEN—Graduation 2000; Collection of Student Projects; Excerpt on Palmi Einarsson's Design Project; Oct. 2000.

* cited by examiner

*Primary Examiner*—Kathleen Mosser
(74) *Attorney, Agent, or Firm*—Bacon & Thomas

(57) ABSTRACT

An educational prosthesis device for a wearer of an upper limb prosthesis that includes a grasping device which extends from a distal portion thereof. The device includes an interactive, computerized system for teaching how to use the prosthesis for manual activities, and a computer including a display and input buttons. A program executable by the computer displays on the display a selection of modules that may be selected by the wearer and provide different interactive education sessions. The device further includes a plurality of instruments attachable onto the grasping elements and which are configured for performing predetermined tasks displayed by the interactive computerized system. The device also may include a protective sleeve having a figurine mounted thereon and a garment sleeve having decorations.

20 Claims, 5 Drawing Sheets

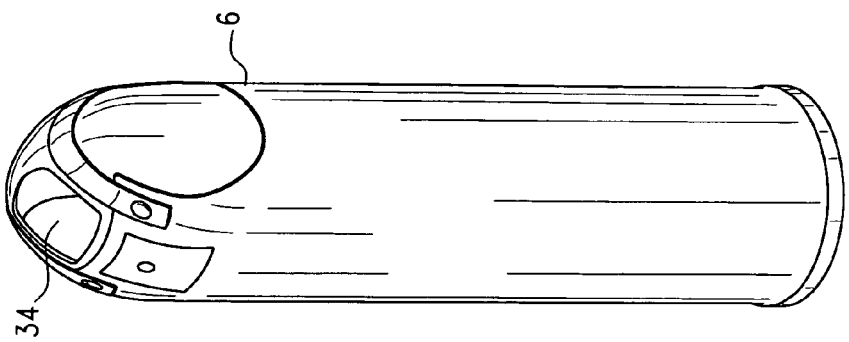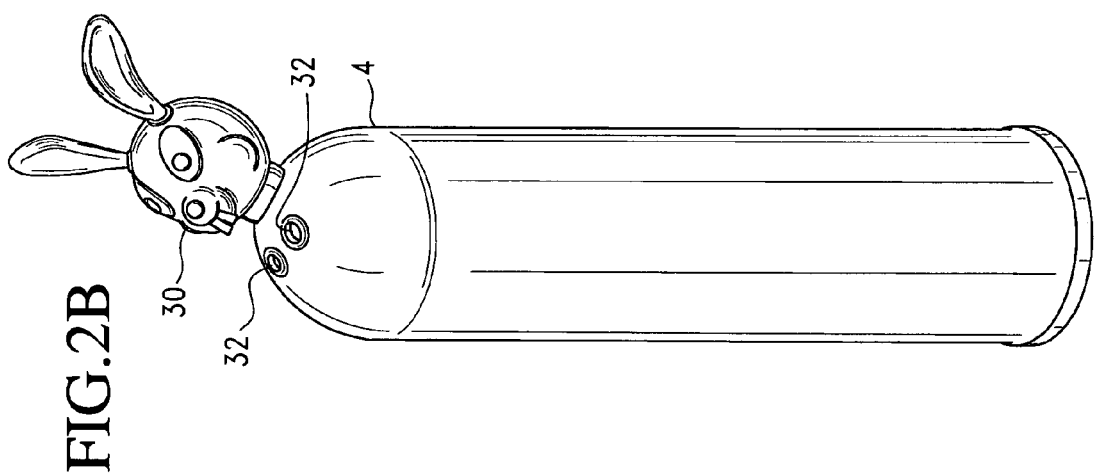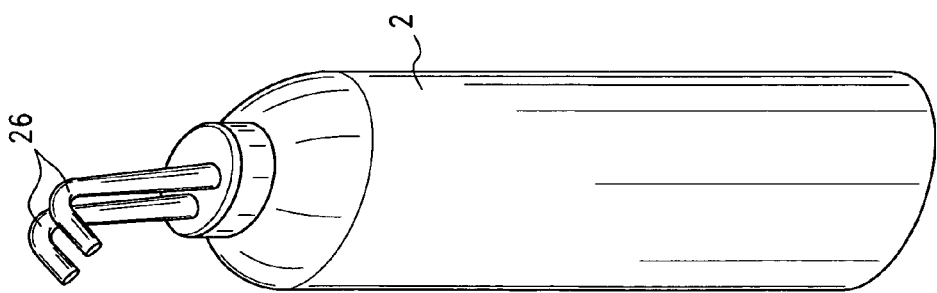

EDUCATIONAL PROSTHESIS DEVICE AND METHOD FOR USING THE SAME

BACKGROUND OF THE INVENTION

1. Field of Art

This invention relates to a device for educating a wearer of an upper limb prosthesis how to use a prosthesis for a variety of manual activities. More particularly, the invention assists children having a limb deficiency to practice functional manual skills with a prosthesis and encourages the use thereof.

2. Description of Related Art

Children with congenital or acquired limb deficiencies often experience difficulties in developing a positive body image. A result of their limb deficiencies results in depression, anxiety, and loss of self-esteem. Self-esteem is an important outcome measure for children with visible physical differences such as a limb deficiency. Self-esteem reflects a child's cognitive appraisal of competence in areas that are deemed important, including scholastic achievement, physical appearance, as well as the support which the child receives from significant others in the environment.

In light of the difficulties in developing a positive body image, it is often difficult to train a child how to use an upper limb prosthesis. Children with an upper limb prosthesis must learn how to perform manual skills and it is essential that children wear their prosthesis and practice use therewith so as to develop such manual skills. Often if the child is not convinced of the necessity and desirability of wearing their prosthesis, and unless the child cooperates in wearing and developing manual skills therewith, the child will reject the prosthesis. Accordingly, children need to learn that wearing a prosthesis is not only acceptable, but wearing a prosthesis is desirable.

Therefore, it would be desirable to provide a device for an upper limb prosthesis which assists in encouraging a child having an upper limb deficiency to wear and practice functional skills with a prosthesis. Further, it is also desirable that the device assists in strengthening the self-esteem of a child wearing the prosthesis. The present invention fulfills these needs and provides further related advantages as described in the following summary.

BRIEF SUMMARY OF THE INVENTION

The present invention contemplates a device for educating a wearer of an upper limb prosthesis, having for example a prosthesis including a pair of grasping elements extending from a distal portion thereof. The device for educating a wearer of the upper limb prosthesis includes an interactive, computerized system for teaching use of the prosthesis. The computerized system includes a computer connected to the prosthesis, a display, at least one actuatable input button, and a computer program stored and configured for execution on the computer. The computer program displays on the display a selection of modules intended for interactive use with a wearer to assist the wearer in learning how to use the prosthesis. Each of the modules is selectable by the wearer and provides different interactive education sessions.

In order to assist in teaching the functionality of the prosthesis, at least two instruments are provided which are configured for attachment onto a respective one of the grasping elements, which typically are hook shaped. The modules of the computerized program instruct usage of corresponding instruments in connection with a manual activity.

So as to appeal to children, the device includes a protective sleeve sized to receive the prosthesis therein and a garment sleeve which covers the protective sleeve. The protective sleeve includes a figurine mounted on a distal portion thereof such that the figurine is positioned near the grasping elements when the protective sleeve is inserted onto the prosthesis. The garment sleeve is sized to receive the protective sleeve with the prosthesis inserted therein. The protective and garment sleeves are decorated in accordance with the figurine.

DESCRIPTION OF THE DRAWINGS

The invention is described in more detail in the following description in conjunction with the appended drawings, wherein:

FIG. 2A illustrates a perspective view of an upper limb prosthesis;

FIG. 2B illustrates a perspective view of the protective sleeve of the present invention having a figurine mounted thereon;

FIG. 2C illustrates a perspective view of the garment sleeve of the present invention;

DETAILED DESCRIPTION OF A PREFERRED EMBODIMENT OF THE INVENTION

Figure 1:
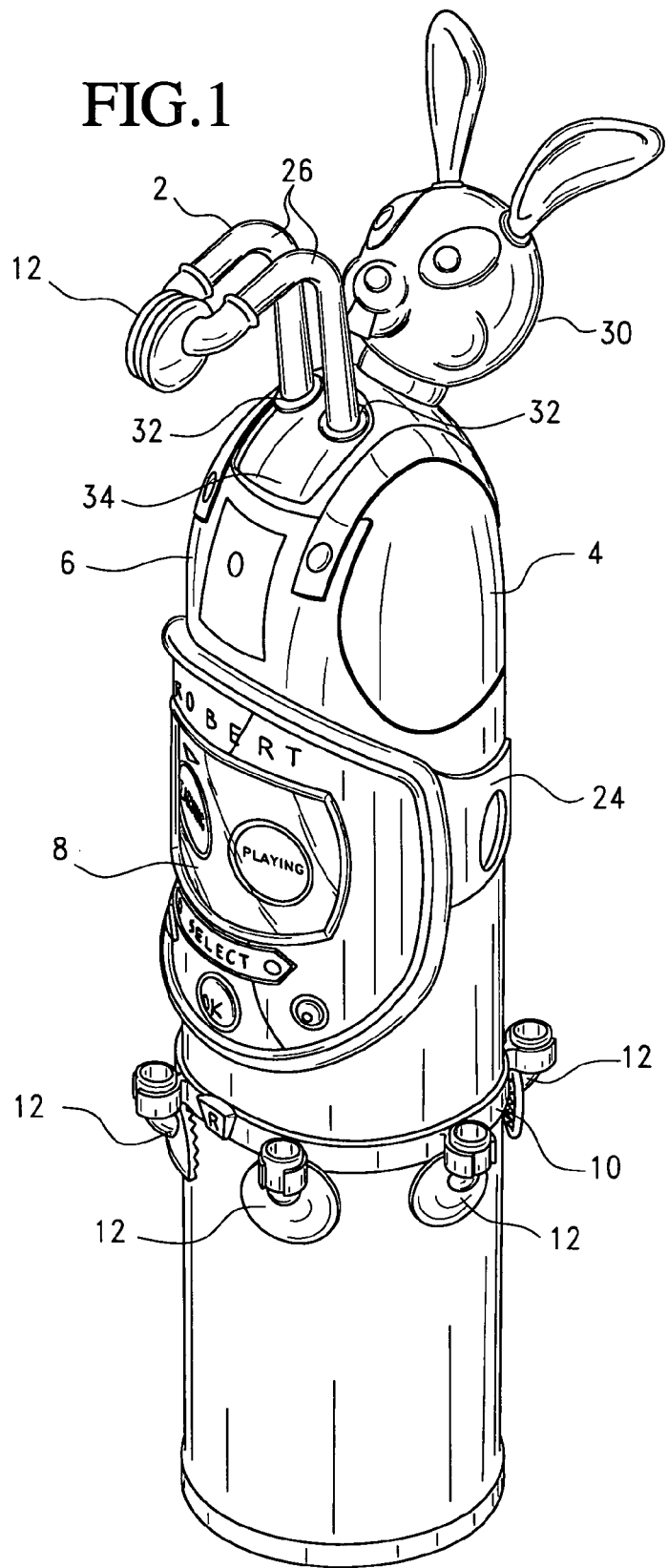
FIG. 1 illustrates a front perspective view of the educational prosthesis device.

FIG. 1 shows a perspective view of the present invention arranged on an upper limb prosthesis 2. The prosthesis includes two hook shaped grasping elements 26 extending from a distal portion thereof. A protective sleeve 4 is sized to receive the prosthesis 2 therein. The protective sleeve 4 has at least one hole defined along a distal portion thereof dimensioned and configured for a respective one of the hook elements 26 to extend therefrom. The protective sleeve 4 includes a figurine 30 mounted on the distal portion thereof. The figurine 30 is positioned near the hook elements 26 when the prosthesis 2 is inserted into the protective sleeve 4. The protective sleeve 4 can be decorated in accordance with the figurine 30.

While the figurine 30 in FIG. 1 is shown in the shape of a rabbit head, it is envisioned that a variety of different figurines can be mounted onto the protective sleeve 4. Such figurines include different types of animals, cartoon characters, miniaturized human heads, sport logos or team mascots, and any other type of representation that appeal to a child.

In the embodiment of FIG. 1, a garment sleeve 6 is placed over the protective sleeve 4 and represents clothing for the figurine 30. The garment sleeve 6 includes an opening 34 which permits the hook elements 26 to extend therefrom.

The device of the present invention includes an interactive, computerized system for teaching use of the prosthesis 2, the system including a computer 8 configured to connect to the prosthesis. In this embodiment, the computer 8 is placed over both the protective sleeve 4 and the garment sleeve 6. The computer 8 includes a clip 24 that is configured to radially clamp onto the prosthesis 2 and to secure the computer 8 thereon.

A mounting belt 10 is configured to connect to the prosthesis 2. The belt is placed over both the protective sleeve 4 and the garment sleeve 6, and supports a plurality of instruments 12 that are configured to connect to a respective one of the hook elements 26.

FIG. 2A depicts a typical upper arm prosthesis 2 having two hook shaped grasping elements 26.

FIG. 2B depicts the protective sleeve 4 having the figurine 30 mounted thereon and openings 32 for hook elements 26 to extend therethrough. In a preferred embodiment the protective layer 4 is constructed from silicone, however any material that will sufficiently cover and serve as a protective layer for the prosthesis can be used.

FIG. 2C depicts the protective garment 6 having an opening 34 that permits the hook elements 26 of an upper arm prosthesis to extend therethrough. In a preferred embodiment the garment layer 6 is constructed from silicone, however any material, such as cloth or paper, that will not harm the protective layer can be used.

Figure 3:
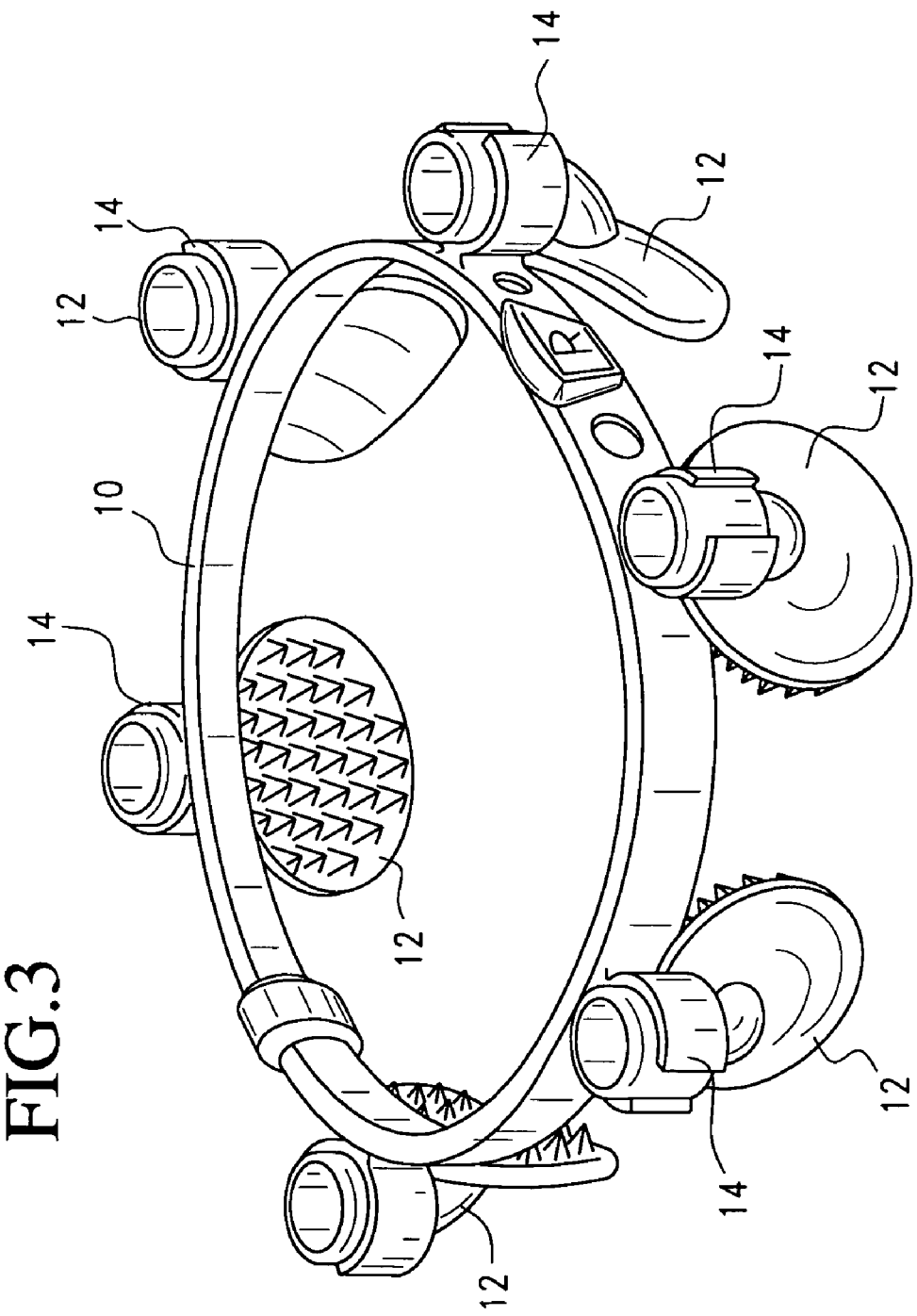
FIG. 3 illustrates a perspective view of the utility belt of the present invention.

FIG. 3 illustrates the utility belt 10 of the present invention. Along the circumference of the belt 10, retainers 14 are positioned which serve to secure the instruments 12 when they are not being used. The belt 10 is configured to circumscribe and radially clamp the prosthesis 2 so as to be secured therewith.

Figure 4:
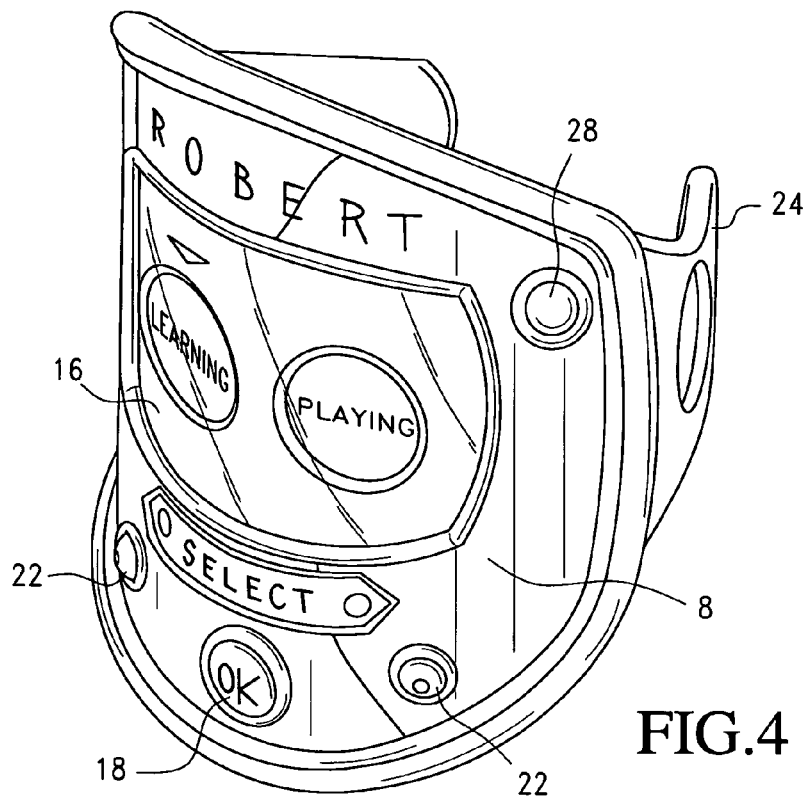
FIG. 4 illustrates a perspective view of the computerized system of the present invention.

FIG. 4 illustrates the interactive, computerized system for teaching use of the prosthesis. The computer 8 includes a display 16 and actuatable input buttons 18, 22. The computerized system further includes a computer program for execution on the computer 8. The computer program displays on the display 16 a selection of modules to assist a wearer in learning how to use of the prosthesis 2 for manual activities. In one exemplary embodiment, the display 16 includes a touch screen.

The computerized system may include an audio speaker 28. In one preferred embodiment, the computerized system provides audio instruction through the speaker 28 to a wearer of the prosthesis on methods of using the prosthesis for predetermined manual activities. The speaker may also produce a sound in response to actuation of the input buttons 18, 22.

In one preferred embodiment of the present invention, the input buttons 18, 22 illuminate upon selection thereof. Furthermore, when only certain buttons 18, 22 are active for selection, such buttons 18, 22 can be configured to illuminate to prompt the wearer for their selection.

Figure 5A:
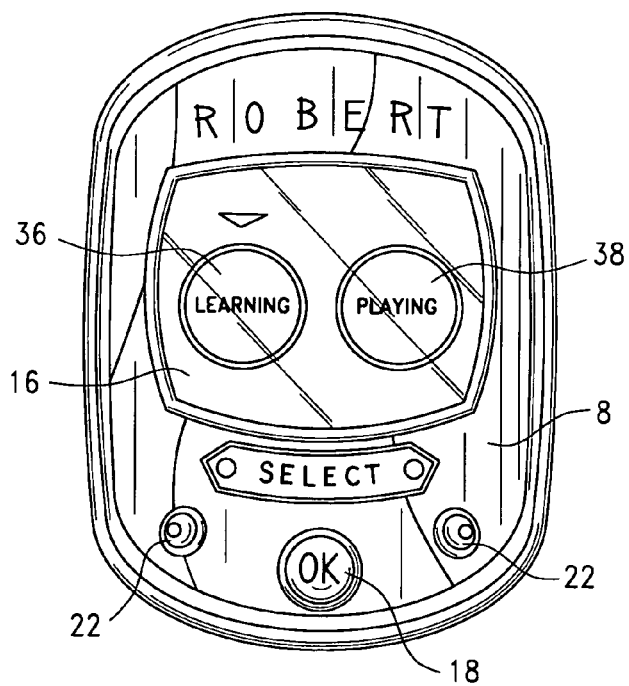
FIG. 5A illustrates a frontal view of the computerized system displaying a query for different modules.
Figure 5B:
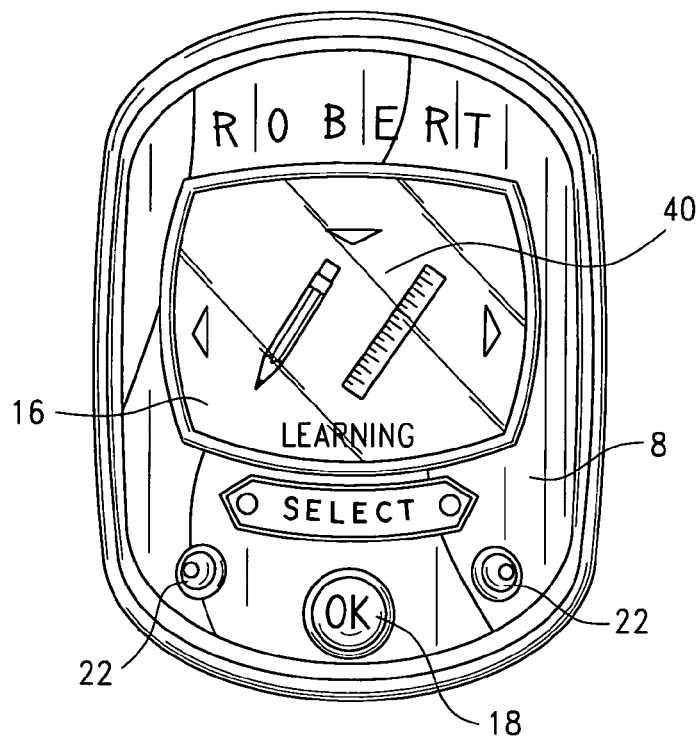
FIG. 5B illustrates a frontal view of the computerized system displaying a query of different manual activities.
Figure 5C:
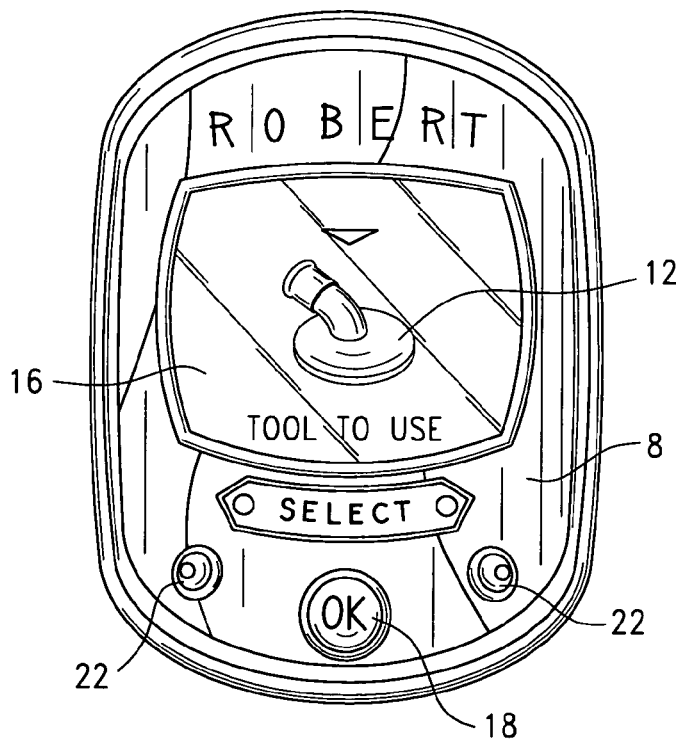
FIG. 5C illustrates a frontal view of the computerized system displaying the appropriate tool for use in a predetermined manual activity.

FIGS. 5A–5C illustrate a method according to the present invention for educating a wearer of an upper limb prosthesis. The method is executed on the interactive, computerized system using computer 8 and suitable software executable and stored therein. FIG. 5A shows the selection of one of the modules 36, 38 corresponding to a particular use of the prosthesis.

Represented in FIG. 5A is a LEARNING module 36 and a PLAYING module 38. The learning module 36 includes a variety of lessons that teach the wearer how to use the prosthesis and the instruments for predetermined manual activities. The playing module 38 includes a series of games that can be played by the wearer. In the present example illustrated in FIG. 5A, the learning module 36 is selected by button 22 and entered by the OK button 18.

In FIG. 5B, after selecting the desired module, the display 16 shows a menu of a variety of manual tasks 40 represented by corresponding figures. The next step is to scroll through the manual activities 40 using buttons 22. The desired manual task is selected by button 18.

FIG. 5C illustrates the display 16 of the computer 8 displaying the appropriate tool 12, TOOL TO USE, for the selected manual activity. Upon displaying the appropriate tool, the wearer attaches the tool 12 corresponding to the tool 12 displayed on the display 16 to one of the grasping elements of the prosthesis.

In addition to showing how to use the tool, the learning module may also include the step of showing on the display how to use the selected tool. The display may show either a picture of the tool being applied for the selected manual activity or animate use of the tool performing the selected activity.

In one preferred embodiment, the computerized system provides an audible sound produced by the speaker 28 when the wearer selects one of the modules and one of the activities. An audible sound is also produced by the speaker 28 when the TOOL TO USE is displayed on the display 16.

Upon selection of the playing module, the display shows games that can be played between the computer and the wearer. In particular, some of the games are programmed to require the wearer to operate the prosthesis in a predetermined manner to provide training and practice for wearing the prosthesis.

Optionally, the software to be installed in the computer may include modules that educate the wearer how to function on a daily basis. Examples include instructing the wearer of appropriate clothes to wear and foods to eat, reminding the wearer that it is time for a nap or a bath, and providing the wearer with an alarm clock.

It will of course be appreciated that the invention is not confined to the particular embodiments described herein, but is intended to embrace all possible variations which might be made to it without departing from either the scope or spirit of the invention as defined in the appended claims.

I claim:

1. A device for educating a wearer of an upper limb prosthesis that includes a grasping device extending from a distal portion thereof, said device comprising:

an interactive, computerized system including a computer that stores and executes at least one program capable of displaying information teaching the use of a prosthesis, the computerized system further including a display and at least one actuatable input button;

a mounting element arranged to mount the computerized system onto a prosthesis;

at least one instrument of a plurality of instruments dimensioned and configured to fit onto a distal end of said grasping device;

wherein the input button is connected to the computer for selection of at least one lesson related to a manual activity of an upper limb prosthesis;

wherein the computer demonstrates on the display how to perform a manual activity corresponding to a selected lesson with an upper limb prosthesis; and wherein said computerized system further includes an executable computer program capable of displaying on said display a selection of modules to interact with a wearer to assist the wearer in learning how to use a prosthesis, said modules being selectable by the wearer for providing different interactive education sessions.

2. The device according to claim 1, wherein the mounting element includes a clamp configured to radially clamp onto a prosthesis and to secure said computer thereon.

3. The device according to claim 1, wherein said computerized system includes an audio speaker.

4. The device according to claim 3, wherein said computerized system includes a program enabling audio instruction to be generated through said speaker to a wearer of a prosthesis related to the use of a prosthesis for manual activities.

5. The device according to claim 4, wherein said program responds to actuation of said at least one input button via said speaker to produce a sound.

6. The device according to claim 1, wherein said at least one input button is illuminated in response to selection of one of said modules.

7. The device according to claim 1, wherein said display comprises a touch screen.

8. The device according to claim 1, including a protective sleeve configured to receive a prosthesis therein, said protective sleeve having at least one opening defined along a distal portion thereof dimensioned and configured to facilitate said grasping device to extend therethrough.

9. The device according to claim 8, wherein the protective sleeve includes a figurine mounted on a distal portion thereof, said figurine being positioned near said grasping device when a prosthesis is received in said protective sleeve, said protective sleeve including decorations selected to be compatible with said figurine.

10. The device according to claim 9, including a garment sleeve configured to receive said protective sleeve when a prosthesis is received by said protective sleeve, said garment sleeve including at least one opening defined along a distal portion thereof dimensioned and configured to enable grasping elements to extend therethrough, said garment sleeve including decorations selected to be compatible with said figurine.

11. The device according to claim 1, wherein said grasping device includes a pair of hook shaped elements, each of said hook shaped elements having one of said instruments connected to a distal portion thereof.

12. The device according to claim 1, wherein each of said education sessions is interactive with one of said instruments, said computer program instructing and displaying how to use at least one of said instruments.

13. The device according to claim 1, including a mounting belt configured to circumscribe and engage a prosthesis, said belt including at least one retainer configured to support said instruments.

14. A method for educating a wearer of an upper limb prosthesis, the upper limb prosthesis including a grasping device extending from a distal portion thereof, at least one instrument connecting onto said grasping device, and an interactive, computerized system mounted on the prosthesis, said computerized system including a computer having a display, at least two actuatable input buttons, and a computer program for execution on said computer, said computer program capable of displaying on said display a selection of interactive modules including information usable by a wearer for learning how to use a prosthesis, said method being executed by the computerized system and comprising the steps of:
  selecting one of said modules, the selected module including a predetermined lesson corresponding to a particular use of the prosthesis;
  displaying on said display a representation of at least two manual activities corresponding to the selected interactive module;
  selecting an activity represented on said display; and
  demonstrating on said display how to perform said selected activity with the prosthesis.

15. The method according to claim 14, wherein said display showing at least one tool usable for said selected activity.

16. The method according to claim 14, wherein said computerized system includes a program generating an audible sound and including the step of generating an audible sound when said wearer selects one of said modules and one of said activities.

17. The method according to claim 14, wherein said computerized system includes an illumination device, and including the step of illuminating one of said input buttons upon selection thereof.

18. The method according to claim 14, further comprising the step of displaying on said display how to use the displayed tool for said selected manual activity.

19. A prosthetic system for educating a wearer of a prosthesis, the system comprising:
  a limb prosthesis; and
  an education device including an interactive, computerized system comprising a display, a selection device and a computer that stores and transmits on the display at least one module including at least one lesson corresponding to a manual activity for use with the prosthesis, the selection device providing input to the computer and permitting selection of the at least one lesson;
  wherein the education device is mounted onto and supported by the limb prosthesis.

20. A method for educating a wearer of a prosthetic system including a limb prosthesis, and an education device mounted onto the prosthesis and including an interactive, computerized system having a computer with a display, the computer storing and executing at least one educational module, the method comprising the steps of:
  displaying the at least one educational module on the display;
  selecting one of the educational modules, the selected educational module including a lesson corresponding to a particular use of a prosthesis;
  displaying on said display a representation of at least one manual activity corresponding to the selected educational module;
  selecting an activity represented on said display; and
  demonstrating on said display how to perform said selected activity with the prosthesis.

* * * * *